(12) United States Patent
Elkin et al.

(10) Patent No.: US 7,251,846 B1
(45) Date of Patent: Aug. 7, 2007

(54) HARNESS FOR SECURING AN INFANT TO REFLUX WEDGE

(75) Inventors: Robynne R. Elkin, Frisco, TX (US); Craig Troop, Frisco, TX (US)

(73) Assignees: CR Enterprises, LLC, Frisco, TX (US); RP Enterprises, LLC, Plano, TX (US)

( * ) Notice: Subject to any disclaimer, the term of this patent is extended or adjusted under 35 U.S.C. 154(b) by 0 days.

(21) Appl. No.: 11/361,527

(22) Filed: Feb. 24, 2006

(51) Int. Cl.
*A47D 13/08* (2006.01)
*A61F 5/37* (2006.01)

(52) U.S. Cl. .............................. 5/655; 5/922; 128/875

(58) Field of Classification Search ................... 5/655, 5/632, 731, 922, 923; 128/875
See application file for complete search history.

(56) References Cited

U.S. PATENT DOCUMENTS

| | | | |
|---|---|---|---|
| 2,404,505 A * | 7/1946 | Knecht ...................... 297/467 |
| 3,099,486 A * | 7/1963 | Scott ......................... 297/465 |
| 3,136,311 A * | 6/1964 | Lewis ........................ 128/874 |
| 3,323,150 A * | 6/1967 | Rehder ...................... 128/872 |
| 4,050,737 A * | 9/1977 | Jordan ....................... 297/465 |
| 4,117,840 A * | 10/1978 | Rasure ....................... 128/874 |
| 4,471,767 A * | 9/1984 | Guimond ...................... 601/5 |
| 4,657,005 A * | 4/1987 | Williamson ................. 128/875 |
| 4,745,926 A * | 5/1988 | Hlusko ....................... 128/873 |
| 4,802,244 A * | 2/1989 | McGrath-Saleh ................ 2/69 |
| 4,862,535 A * | 9/1989 | Roberts ........................ 5/655 |
| 4,911,105 A * | 3/1990 | Hocum ........................ 128/875 |
| 4,989,286 A * | 2/1991 | Tucker ......................... 5/482 |
| 5,208,925 A * | 5/1993 | Edlund ......................... 5/424 |
| 5,233,714 A * | 8/1993 | De Bell Daniel ................ 5/655 |
| RE34,763 E | 10/1994 | Tucker ......................... 5/482 |
| 5,439,008 A * | 8/1995 | Bowman ....................... 5/655 |
| 5,440,770 A * | 8/1995 | Nichols ........................ 5/655 |
| 5,700,059 A * | 12/1997 | Moscot ........................ 5/655 |
| 6,381,785 B1 * | 5/2002 | Mancera Browne et al. ... 5/655 |
| 6,708,356 B1 * | 3/2004 | LaValle ........................ 5/655 |
| 6,837,880 B2 * | 1/2005 | Trimble ...................... 604/393 |
| 6,922,861 B1 * | 8/2005 | Mathis ......................... 5/655 |
| 6,931,683 B1 | 8/2005 | Elkin et al. .................... 5/655 |
| 7,003,831 B1 * | 2/2006 | Goutevenier-Reyher ....... 5/655 |
| 2005/0198739 A1 * | 9/2005 | Elkin et al. .................... 5/655 |

* cited by examiner

*Primary Examiner*—Robert G. Santos
(74) *Attorney, Agent, or Firm*—Michael Diaz

(57) ABSTRACT

A harness for positioning and securing an infant to a reflux wedge. The harness includes a crotch support having a front flap and a rear flap connected to each other by a transverse section. Two straps extend upward from the rear flap. An infant is placed in the harness and secured to the reflux wedge. The infant's position (up or down) on the surface of the reflux wedge is fully adjustable. The straps are affixed to a horizontal slit found in the main body of the reflux wedge by hook and pile material. The straps are attached to each other by a material section. The harness prevents the infant from slipping down the slope of the wedge. The unique design of the wedge and harness allows for either prone or supine positioning of the infant. Infant shoulder protraction is facilitated in either the prone or supine position when the infant rests within the harness attached to the wedge.

10 Claims, 7 Drawing Sheets

US 7,251,846 B1

HARNESS FOR SECURING AN INFANT TO REFLUX WEDGE

BACKGROUND OF THE INVENTION

1. Field of the Invention

This invention relates to harnesses. Specifically, and not by way of limitation, the present invention relates to a harness for securing an elevated recumbent infant to an infant reflux wedge.

2. Description of the Related Art

Gastroesophageal Reflux Disease, also know as GERD, is a common ailment which results from a back flow (reflux) of acid from the stomach into the esophagus. This acid can irritate or even damage the delicate lining on the inside of the esophagus. The usual symptom is heartburn, which is an uncomfortable burning sensation behind the breastbone. In some individuals this reflux is frequent enough to cause more significant problems, resulting in GERD. Thus, GERD is a clinical condition that occurs when reflux of stomach acid into the esophagus is severe enough to impact the patient's life and/or damage the esophagus. Infants are susceptible to GERD and suffer tremendously from its effects.

Standard protocol for alleviating the symptoms of an infant with GERD is to elevate the recumbent infant approximately 30 to 45 degrees. The infant is often placed on a wedged-shaped mattress. The infant is positioned at an inclined angle to reduce the volume or amount of refluxed gastric fluid. The infant is held in place by a sling or harness device. The elevated positioning of the infant is very helpful. Typically, the infant is laid face down in a prone position for improved gastric emptying or for more effective results. However, simply laying an infant on either his back or stomach on a flat surface results in some very significant musculoskeletal problems associated with the prolonged use of the elevated mattress. In particular, the shoulders of the infant tend to retract backwards. With the prolonged use of the elevated mattress, the infant is not able to protract (move forward) his shoulders. The lack of an ability for the infant to protract his shoulders is detrimental to the musculoskeletal development of the infant. A device is needed which enables the infant to enjoy the benefits of the inclined position on a wedge apparatus without positioning the infant in such a manner as to encourage retraction of the shoulders.

U.S. Pat. No. 6,931,683 to Elkin et al. (Elkin) discloses a novel advanced infant reflux wedge which solves the problems associated with existing devices. However, to provide a hygienic and comfortable apparatus, the wedge is preferably covered in a smooth medical grade vinyl material. Because of the smoothness of the material and the elevation of the wedge, the infant often slides down the wedge, thus defeating the purpose of the wedge. A device is needed to secure the infant on the wedge and prevent the infant from sliding down the slope of the wedge.

Although there are no known prior art teachings of a solution to the aforementioned deficiency and shortcoming such as that disclosed herein, prior art references that discuss the subject matter bears some relation to matters discussed herein is U.S. Pat. No. Re. 34,763 to Tucker (Tucker). Tucker discloses a bedding article for supporting an infant with gastroesophageal reflux. A covering is placed over the crib mattress and forms a tensile load carrying connection band. An infant support sling is then connected to the band. The Tucker sling and elevated mattress can cause the aforementioned problem of shoulder retraction. The sling disclosed in Tucker also suffers from several other disadvantages. The Tucker sling requires attachment to a bedding article such as a mattress cover which is not available for the wedge disclosed in Elkin. In addition, the sling disclosed in Tucker does not provide for adjustment in height to properly align the infant in the wedge. The Tucker sling merely provides a device to secure an infant in an elevated bed. The Tucker sling cannot be utilized on the reflux wedge disclosed in Elkin.

Thus, it would be a distinct advantage to have a fully adjustable harness which safely and comfortably secures an infant to a reflux wedge such as disclosed in Elkin. It is an object of the present invention to provide such an apparatus.

SUMMARY OF THE INVENTION

In one aspect, the present invention is a harness for securing an infant to an inclined surface. The harness includes a crotch support having a rear flap with a first side and a second opposite side, a front flap, and a transverse section connecting the rear flap to the front flap. Two straps extend from the top of the rear flap. The two straps are attached to the inclined surface. The infant is positioned within the crotch support with the front flap being positioned over the top of the crotch of the infant and attached to the rear flap and the straps being attached to hook and pile material located within the slit of the wedge.

In another aspect, the present invention is a combination harness and reflux wedge. The combination includes an infant reflux wedge having an inclined surface and a harness for securing an infant to the wedge. The harness has a crotch support with a rear flap that has a first side and a second opposite side. The crotch support also has a front flap and a transverse section connecting the rear flap to the front flap. The front flap is connected to the rear flap when the infant is secured in the harness. Two straps extend from the top of the rear flap. The two straps are attached to the wedge surface. The infant is positioned within the crotch support with the front flap being positioned over the top of the crotch of the infant and attached to the rear flap and the straps being attached to a slit located within the wedge.

BRIEF DESCRIPTION OF THE DRAWINGS

The invention will be better understood and its numerous objects and advantages will become more apparent to those skilled in the art by reference to the following drawings, in conjunction with the accompanying specification, in which.

DESCRIPTION OF THE INVENTION

Figure 1:
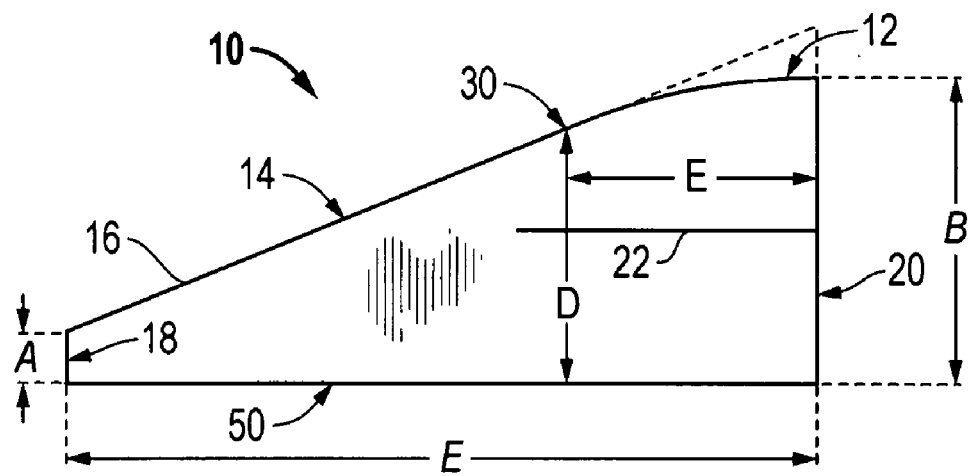
FIG. 1, a side view of an infant reflux wedge.

A harness for securing an infant to an infant reflux wedge is disclosed. FIG. 1 is a side view of an infant reflux wedge 10. The reflux wedge 10 includes a head support region 12 and a torso support region 14 located on a top side 16. The reflux wedge is dimensioned with a bottom end section 18 having a height A of between one and two inches. On an opposite head end section 20, the head reaches a height B of approximately 12 inches. Approximately halfway down the height B is a horizontal cut 22 running the width F of the wedge. Preferably, the horizontal cut has a length or depth of approximately 12 inches.

The head support region 12 is curvilinear-shaped starting at distance C of approximately 10 inches from the head end section 20. The head support region, at an intersection point 30, is approximately a height D of approximately 10 inches above a horizontal surface on which the reflux wedge lies. FIG. 1 depicts a dashed line to illustrate that the head support region curves to a relatively horizontal orientation rather than continuing the angular inclination of the top side of the torso support region. The head of an infant is positioned in a prone (stomach/abdomen down) position upon the head support region.

The torso support region 14 is sized and shaped to provide an incline between approximately 15 and 45 degrees. The torso and legs of the infant (prone position) are positioned on the torso support region.

The reflux wedge 10 preferably comprises a structural plastic foam such as a foam polyurethane material, urethane foam, or other elastomeric material. The foam used may consist of a variety of colors and may comprise a variety of different densities that determine the hardness or softness of the wedge 10. The foam may also possess anti-static properties and may be latex free.

More specifically, Indentation Force Deflection (IFD) measures the firmness of a piece of foam. The test involves placing a 4"×15"×15" piece of foam on a flat surface. A round metal piece, 8" in diameter, pushes down on the piece of foam. The amount of pounds of pressure required to squeeze the piece of foam from 4" to 3" is the IFD. Preferably, the reflux wedge 10 of the present invention has an IFD of between about 22 and 42.

Additionally, the State of California Bureau of Home Furnishings Technical Bulletin #117 (bulletin #117) requires that all foam sold in retail in the state of California must pass a fire retardant test. The test involves exposing a piece of foam to an open flame until the foam is burning. Once the foam is burning, the foam is removed from the flame. Fire retardant foam ceases to burn once removed from the flame. Preferably, since California is such a large market, the wedge 10 meets bulletin #117. Likewise, it is desirable that the foam type meets or exceeds the requirements of FAA (Federal Aviation Administration) 25.853(a) App. F Part I(a)(1)(ii). This section refers to a 12 second vertical hang burn test.

The reflux wedge 10 may comprise a variety of elastomeric materials. For example, a white J32 foam type having a density of 0.90–0.95 and an IFD of 29.0–36.0 may be employed. Alternatively, a blue L32XB foam type having a density of 1.20–1.26 and an IFD of 32.0–37.0 that exceeds California Bulletin #117 flammability requirements may be employed. Alternatively, a pink P25T foam type having a density of 1.20–1.26 and an IFD of 24.0–29.0 may be employed. The interior of the reflux wedge includes this foam. The foam is typically covered with a smooth material such as vinyl.

Figure 2:
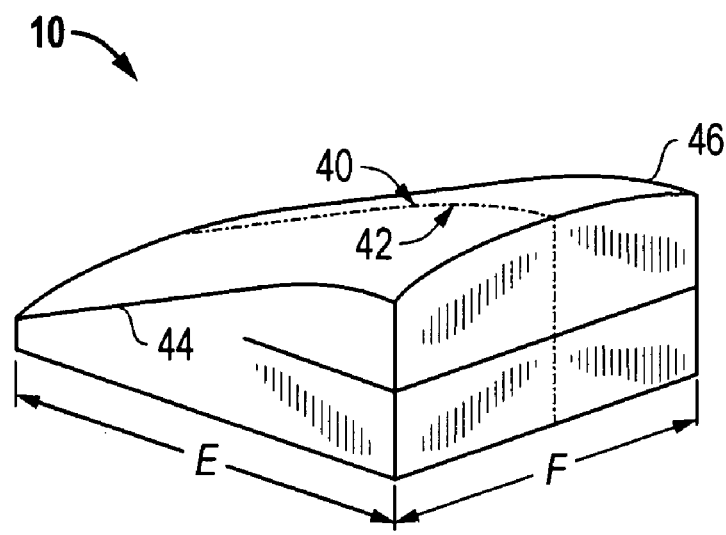
FIG. 2 is a top perspective view of the infant reflux wedge of FIG. 1.

FIG. 2 is a top perspective view of the infant reflux wedge 10 of FIG. 1. The reflux wedge is constructed with an arch 40 running down a midline 42 of the wedge. The arch slopes downward from the midline to sides 44 and 46. The arch slopes downward from the midline to each side of the wedge by a height of approximately one to three inches. The arch may run the full length of the width or approximately ¾ of the length of the wedge. In addition, the arch may or may not be located on the head support region.

The length E of the wedge is preferably between 26 and 30 inches. The width F of the wedge is preferably about 24 inches. The dimensions are preferred. It should be understood that the wedge may be decreased or increased in size and still provide the same function. In addition, the angle of the wedge is preferably configured to incline the torso of the infant between 30 and 40 degrees, however the incline may range from 15 degrees to 45 degrees.

Figure 3:
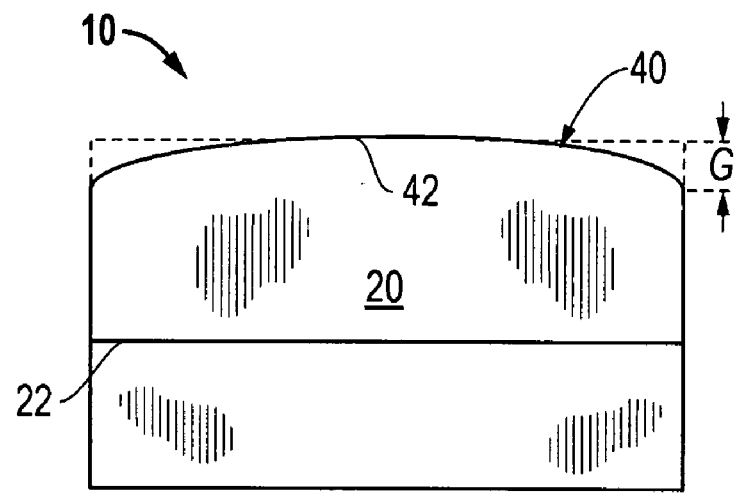
FIG. 3 is a view from the head end section of FIG. 1.

FIG. 3 is a view from the head end section 20 of FIG. 1. FIG. 3 illustrates the arch 40 located at the midline 42. The arch slopes down from the midline to the sides 42 and 44 a distance G, which is approximately between one and three inches.

Figure 4:
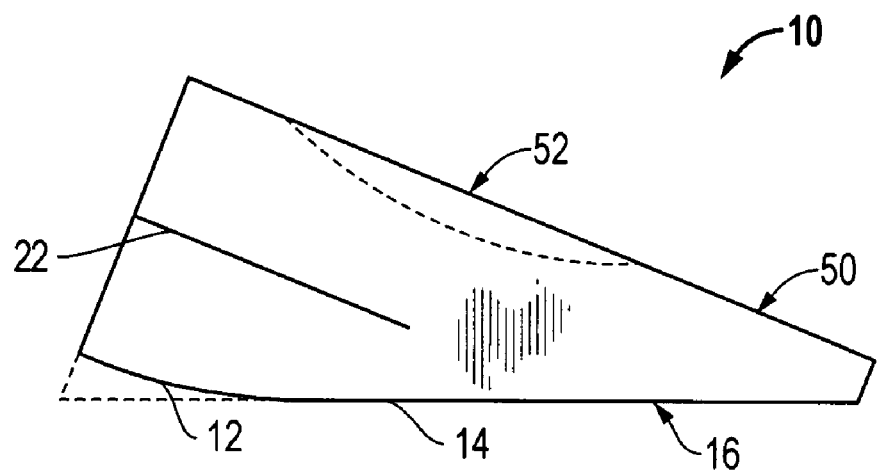
FIG. 4 is a side view of the infant reflux wedge flipped over with a bottom side having a nest facing upward.

FIG. 4 is a side view of the infant reflux wedge flipped over with a bottom side 50 and a nest 52 facing upward. The infant reflux wedge may optionally include the shallow concave nest 52 upon the bottom side of the wedge. When the infant reflux wedge is flipped over and the bottom side is facing upward, the nest 52 is exposed.

Figure 5:
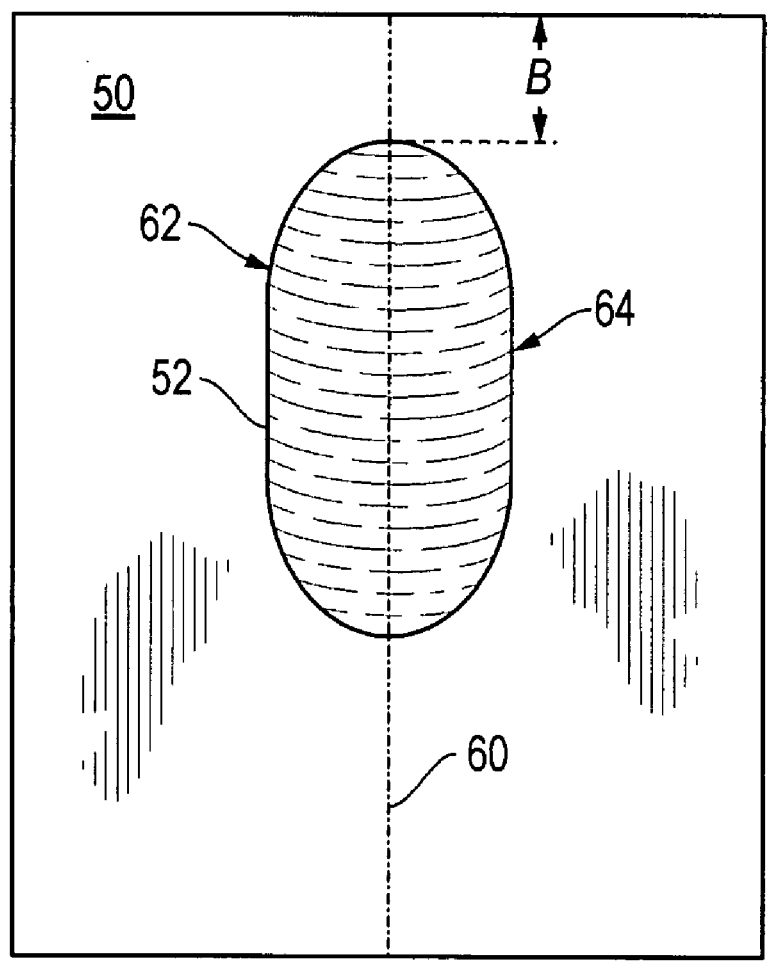
FIG. 5 is a top view of the bottom side of the infant reflux wedge illustrating the nest.

FIG. 5 is a top view of the bottom side of the infant reflux wedge 10 illustrating the nest. The nest is a hollowed out area preferably having the shape of an oval and having a gradual sloping from a midline 60 to its outer sides 62 and 64. The deepest portion of the nest is at the midline 60 where the depth is approximately one to three inches. The nest is preferably positioned a distance H of approximately four inches from the head end section 20. The nest also preferably has a length of approximately 18 inches and a width of 12 inches. However, the size and placement of the nest may vary. With the bottom side facing upward (FIG. 5), the infant is positioned in a supine position (face up) within the nest 52.

With reference to FIGS. 1–5, the operation of the infant reflux wedge 10 will now be explained. To alleviate symptoms from GERD, infants are inclined at an angle between 30 and 45 degrees. The infant may be positioned in a prone (stomach/abdomen down) position on the top side 16. The infant is positioned so that the infant's head lies to either side on the head support region 12. The remaining portion of the infant (torso and legs) is positioned on the torso support region 14. The infant is positioned so that the infant essentially straddles the arch, thereby allowing or encouraging the shoulders of the infant to lie in a forward or protracted position. Thus, it is imperative that the infant be positioned and stabilized in a position to straddle the arch and allow or encourage the shoulders of the infant to lie in a forward position. In addition, since the head support region is curvilinear, the infant may comfortably lay his head upon the head support region.

Although it is recommended that an infant suffering from GERD be positioned in a prone position, parents may wish to position the infant on his back. If it is desired to lay the infant on his back (supine position), the infant reflux wedge may be flipped over to a position where the bottom side 50 is facing upward (FIGS. 4 and 5). The infant is positioned in the nest 52, allowing the infant to "nestle" within the nest. In such a position, the infant's shoulders are lifted upward into a protracted position which promotes slight flexion of the upper and lower extremities. The nest will also provide the infant with a boundary for comfort and containment. In addition, with the head support region contacting the horizontal surface on which the wedge is placed, a rocking motion of the wedge may be initiated (similar to a rocking chair).

Utilization of either side of the infant reflux wedge encourages protraction of the infant's shoulders, slight flexion of the upper and lower extremities and discourages retraction of the shoulders. With the infant reflux wedge, the infant can comfortably utilize an inclined surface to alleviate symptoms associated with GERD while simultaneously reducing or eliminating the problems of the infant's muscular development associated with prolonged use of an inclined flat surface. The infant reflux wedge allows the infant to rest his head comfortably upon the curvilinear-shaped head support region.

Figure 6:
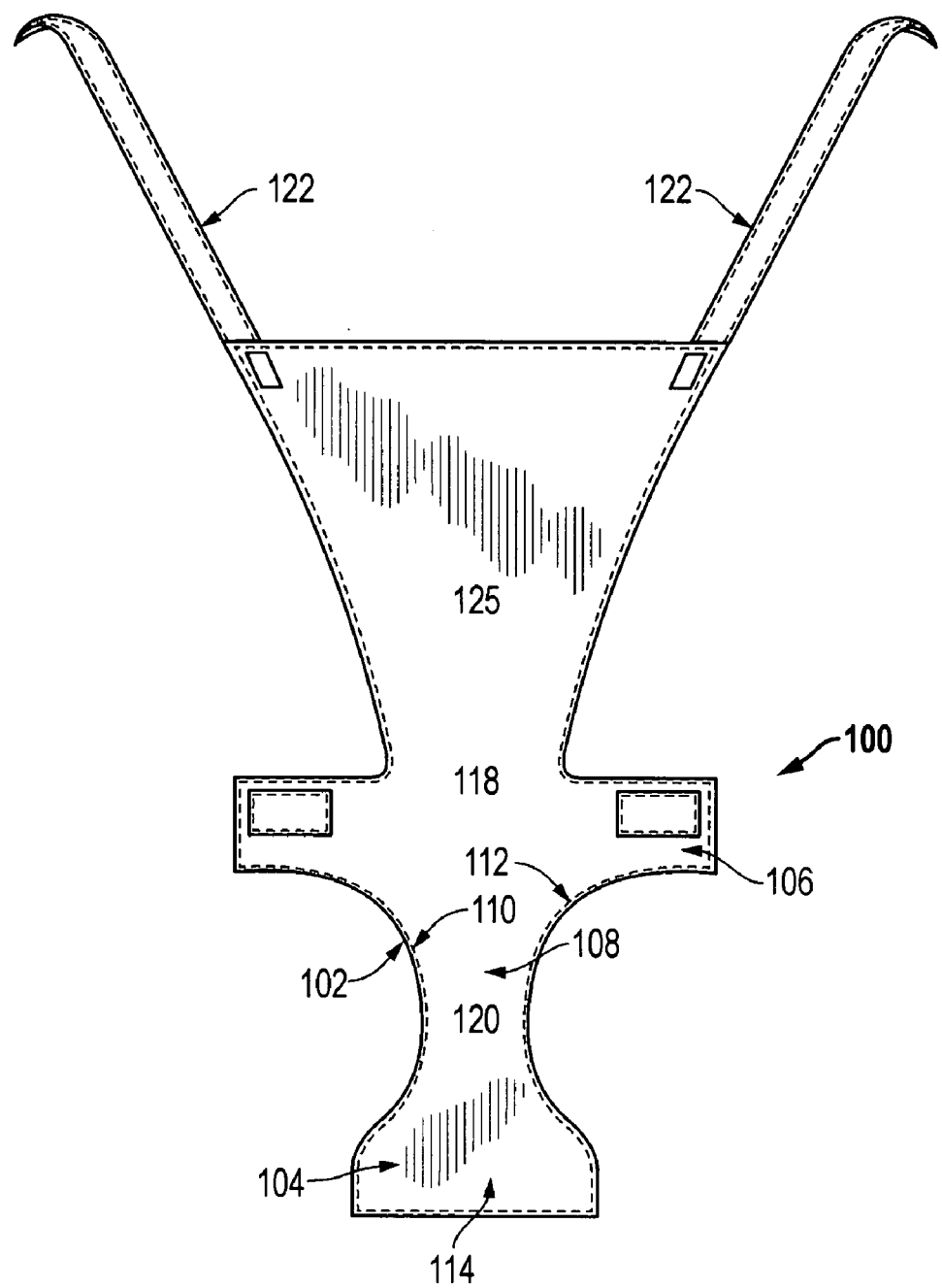
FIG. 6 is a top view of the harness laying flat for use with the reflux wedge.
Figure 7:
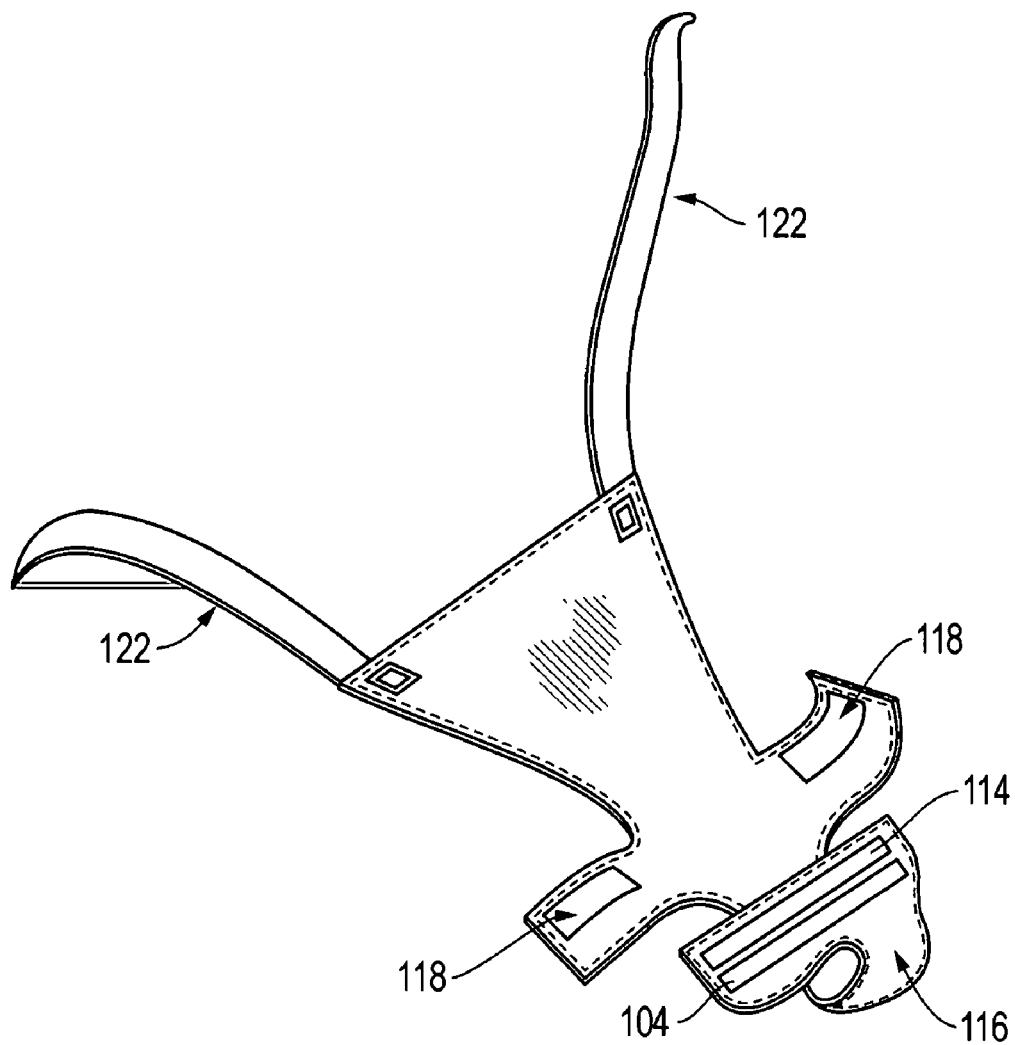
FIG. 7 is a top perspective view of the harness of FIG. 7 with the front flap turned up.

As discussed above, the position upon the infant reflux wedge is critical to the function of the wedge. To prevent sliding of the infant down the slope of the wedge, a harness 100 is utilized. FIG. 6 is a top view of the harness 100 laying flat for use with the reflux wedge 10. FIG. 7 is a top perspective view of the harness 100 of FIG. 6 with the front flap turned up. The harness includes a crotch support section 102 having a front flap 104 and a rear flap 106. The front and rear flaps are connected by a transverse section 108. Preferably, the transverse section includes a curved outline on a side 110 and side 112 to accommodate the infant's legs. Hook strips 114 may be affixed to a back side 116 (FIG. 7) of the harness on the front flap. Additionally, corresponding pile strips 118 may be affixed to a top side 120 of the rear flap 106. The rear flap includes sides sized to fit over the top of an infant. Affixed to the rear flap are two elongated straps 122. Each elongated strap is preferably constructed of a hook or pile material. The straps are connected to each other by a material section 125 which is attached to both straps and extends down to the top of the rear flap 106. Preferably, the material section is constructed of a canvas. The harness 100 is preferably constructed of a strong, flexible, washable material.

Figure 8:
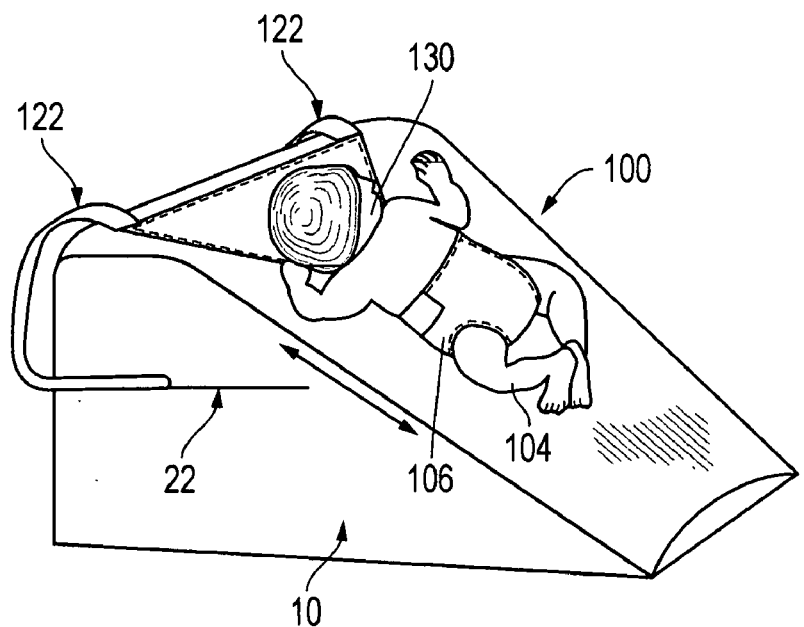
FIG. 8 is a front perspective view of an infant positioned prone (face down) within the harness on the infant reflux wedge in the preferred embodiment of the present invention.

FIG. 8 is a front perspective view of an infant 130 positioned in the prone position within the harness 100 on the infant reflux wedge 10 in the preferred embodiment of the present invention. The front flap 104 is turned up over the front portion of the infant's crotch. The two sides of the rear flap 106 are wrapped over the front flap and secure the infant in place within the harness. The flaps are held against each other by the hook and pile strips. The hook and pile strips may be positioned on any surface to allow secure placement of the flaps against each other. Any attachment devices may be utilized, such as buckles, snaps, buttons, etc. The crotch support section is similar to other harness devices which provide support to a person's crotch. The straps 122 are affixed to the rear flap and run underneath the infant and extend upwards beyond the infant's shoulders and attached into the slit of the wedge. Thus, the straps do not hang over the infant's shoulders and cause discomfort to the infant.

Figure 9:
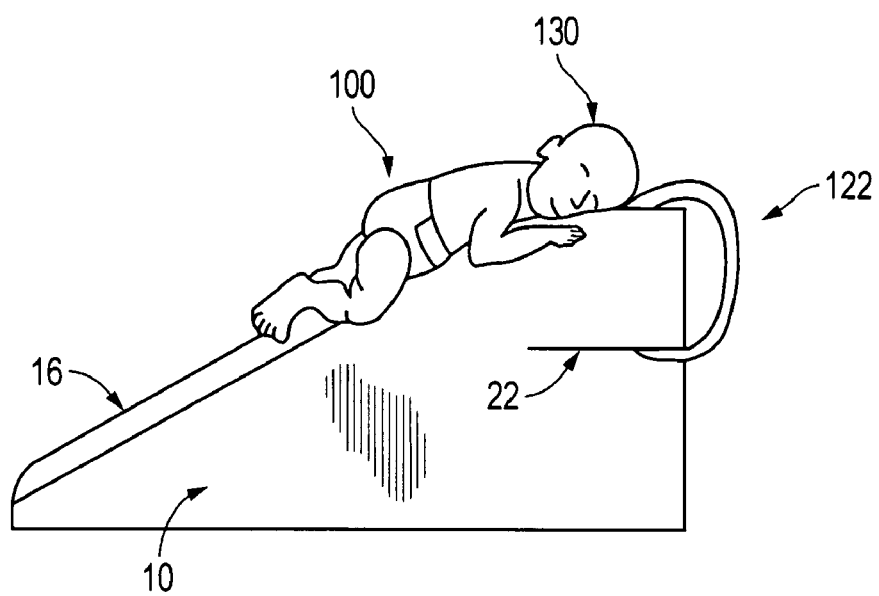
FIG. 9 is a side view of the harness holding the infant on the infant reflux wedge lying prone on the top side of the infant reflux wedge.

FIG. 9 is a side view of the harness 100 holding the infant 130 lying in the prone position on the top side of the infant reflux wedge 10. The straps 122 are positioned over the top of the infant reflux wedge 10 and positioned within the horizontal cut 22. As discussed above, the placement of the infant on the wedge 10 is critical. The straps 122 may be positioned deeper within the horizontal cut as necessary to slide the infant further up the slope of the wedge. Likewise, if desired, the strap may be positioned close to the edge of the slit, thereby sliding the harness further down the slope of the infant reflux wedge. The straps are held in place within the horizontal slit by hook and pile strips. In the preferred embodiment of the present invention, the strap may be constructed of hook material while each side of the slit may include pile material. When the strap is inserted within the slit, the strap is securely held in place by the corresponding pile material and the weight of the top of the wedge on the slit. FIGS. 8 and 9 depict the infant in the prone position.

Figure 10:
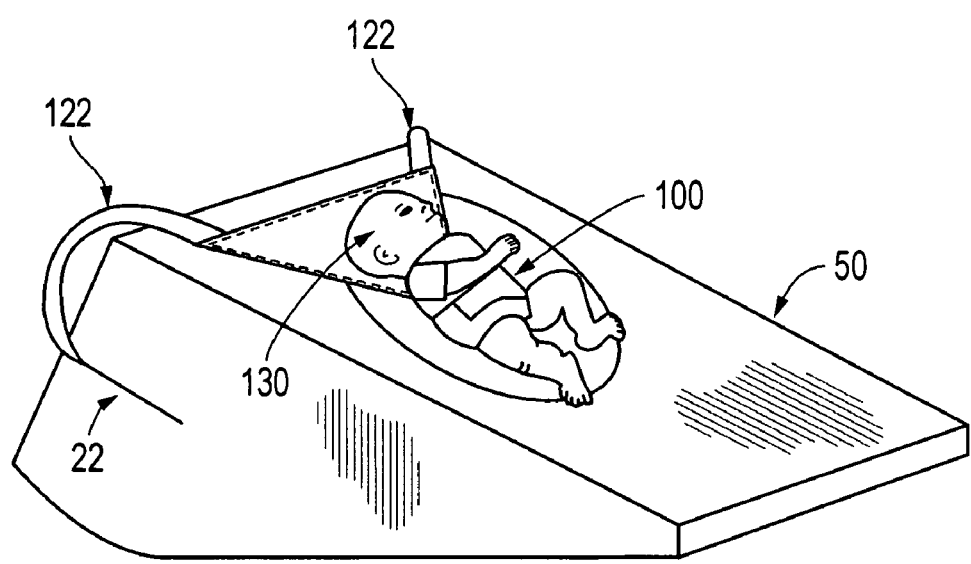
FIG. 10 is a side perspective view of the harness holding the infant in the supine (face up) position, which is the bottom side of the reflux wedge.

FIG. 10 is a side perspective view of the harness 100 holding the infant in the supine position on the bottom side of the reflux wedge 10. The harness is designed to be utilized on either side without modification to the wedge or harness to accommodate the infant in the prone or supine position.

With reference to FIGS. 1–10, the operation of the harness upon an infant reflux wedge will now be explained. The harness 100 is positioned on the top surface of the infant reflux wedge 10. The straps 122 are positioned over the top uppermost portion of the wedge and secured within the horizontal slit 22. The straps are held in position by the hook and pile strips on the straps and within the slit. The infant is positioned at the proper height on the wedge to provide all the functions and benefits of the infant reflux wedge. The front flap 104 is pulled up over the front of the pelvis of the infant and secured by hook and pile strips to the sides of the rear flap 106. The material section 125 is preferably used to prevent the straps from sliding off the sides of the wedge. Additionally, the infant's head is positioned on top of the material section 125 to provide protection and comfort for the infant as the infant lies against the sloped surface of the reflux wedge.

The present invention may be used on any wedge having a slit running through a portion of the wedge. Additionally, the harness may be secured to the infant and the wedge by any attachment means, such as buttons, snaps, buckles, etc.

The harness provides many advantages over existing harnesses. The present invention enables the position of an infant to be adjusted along the slope of a sloped surface. Additionally, the present invention prevents the straps from sliding off the sides of the wedge. The harness is securely fastened to the wedge and does not require additional bedding or devices to secure the harness to the wedge. The harness is also reversible, allowing the infant to be positioned on either the top side or bottom side of the wedge to accommodate either an infant in the prone or supine position.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A harness for securing an infant to an inclined surface; the harness comprising:
    a crotch support having:
        a rear flap with a first side and a second opposite side;
        a front flap;
        a transverse section connecting the rear flap to the front flap;
        means for attaching the front flap to the rear flap; and
    two straps extending from a top of the rear flap and extending over a top edge of the inclined surface, the two straps having attaching means for attaching the two straps to the inclined surface;
    wherein the inclined surface is an infant reflux wedge and the infant is positioned on the inclined surface at a position to benefit from the infant reflux wedge, the wedge having a slit in a portion of the wedge and the attaching means for attaching the two straps to the inclined surface includes means for attaching the straps within the slit;
    wherein the straps include a hook or pile material and the slit includes a correspondingly opposing pile or hook material to attach the straps to the wedge;
    whereby the infant is positioned within the crotch support with the front flap being positioned over the top of the crotch of the infant and attached to the rear flap and the straps being attached to the inclined surface.

2. The harness for securing an infant to an inclined surface of claim 1 wherein the straps are positioned under the infant without being positioned over a chest of the infant.

3. The harness for securing an infant to an inclined surface of claim 1 wherein the straps include a material section connecting the two straps together.

4. The harness for securing an infant to an inclined surface of claim 1 wherein sides of the rear flap are sized to fit over the infant.

5. The harness for securing an infant to an inclined surface of claim 4 wherein the means for attaching the front flap to the rear flap is hook and pile strips attached to the front flap and the rear flap.

6. The harness for securing an infant to an inclined surface of claim 1 wherein the two straps having attaching means for attaching the two straps to the inclined surface includes means for moving a position of the crotch support upon the inclined surface to properly position the infant upon the inclined surface.

7. A combination harness and reflux wedge, the combination comprising:
    a wedge having an inclined surface; and
    a harness for securing an infant to the wedge, the harness having:
        a crotch support having:
            a rear flap having a first side and a second opposite side;
            a front flap;
            a transverse section connecting the rear flap to the front flap;
            means for attaching the front flap to the rear flap; and
        two straps extending from a top of the rear flap and extending over a top edge of the inclined surface, the two straps having attaching means for attaching the two straps to the wedge;
        wherein the wedge includes a slit in a portion of the wedge and the attaching means for attaching the two straps to the inclined surface includes means for attaching the straps within the slit and the straps include a hook or pile material and the slit includes a correspondingly opposite pile or hook material to attach the straps within the slit of the wedge;
        whereby the infant is positioned within the crotch support with the front flap being positioned over the top of the crotch of the infant and attached to the rear flap and the straps being attached to the inclined surface.

8. The combination harness and reflux wedge of claim 7 wherein the wedge includes:
    a wedge-shaped main body having a top side and a bottom side;
    a torso support section providing a substantially flat and arched incline to receive and support the torso of the infant lying in a prone position, the torso support section located on the top side of the wedge-shaped main body;
    a head support section adjoining the torso support section for receiving and supporting the head of the prone infant, the head support section being curvilinear and substantially horizontal and located on the top side of the wedge-shaped main body; and
    an arch running down a longitudinally aligned midline on the top side for receiving and supporting the prone infant and encouraging protraction of the shoulders.

9. The combination harness and reflux wedge of claim 8 wherein the two straps having attaching means for attaching the two straps to the wedge includes means for moving a position of the crotch support to properly position the infant upon the wedge to encouraging protraction of the shoulders.

10. The combination harness and reflux wedge of claim 7 wherein the bottom side includes a nest to accommodate the infant in a supine position.

* * * * *